United States Patent [19]

Goble

[11] Patent Number: 4,985,032

[45] Date of Patent: Jan. 15, 1991

[54] DRILL GUIDE

[76] Inventor: E. Marlowe Goble, 850 East 1200 North, Logan, Utah 84321

[21] Appl. No.: 522,743

[22] Filed: May 14, 1990

[51] Int. Cl.$^5$ .............................................. A61F 5/04
[52] U.S. Cl. ......................................... 606/96; 606/98
[58] Field of Search ...................... 606/96, 97, 80, 98, 606/104, 75; 411/174, 175; 403/395, 398

[56] References Cited

U.S. PATENT DOCUMENTS

| | | | |
|---|---|---|---|
| 1,670,521 | 5/1928 | Ray | 403/395 |
| 3,535,751 | 10/1970 | Batchelor | 403/395 |
| 3,755,860 | 9/1973 | Schenk | 403/398 |
| 4,672,957 | 6/1987 | Hourahane | 606/96 |
| 4,708,139 | 11/1987 | Dunbar, IV | 606/96 |
| 4,781,182 | 11/1988 | Purnell | 606/96 |
| 4,826,375 | 5/1989 | Holton | 411/174 |
| 4,920,958 | 5/1990 | Walt | 606/96 |

Primary Examiner—Robert A. Hafer
Assistant Examiner—Michael Brown
Attorney, Agent, or Firm—M. Reid Russell

[57] ABSTRACT

A drill guide for drilling a transverse hole in a patient's knee to intersect a bony ligament tunnel formed in an arthroscopic surgical procedure for replacing the patient's cruciate ligament. The drill guide is U-shaped having spaced apart parallel co-planar legs extend from an arcuate base, one of which legs is solid to fit within the bony ligament tunnel and the other is holed at spaced intervals, the longitudinal axis of which holes point towards the solid leg, a select hole to receive a barrel turned therethrough that was an open longitudinal bore to guide a conventional drill turned therethrough and into the patient's knee to intersect, at a right angle, the bony ligament tunnel.

5 Claims, 1 Drawing Sheet

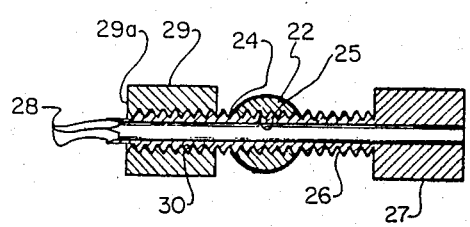
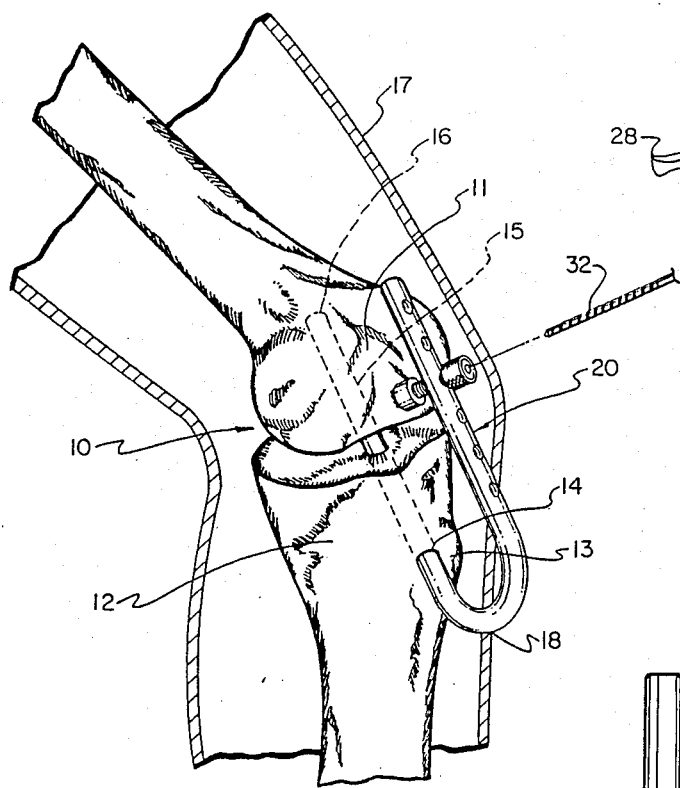
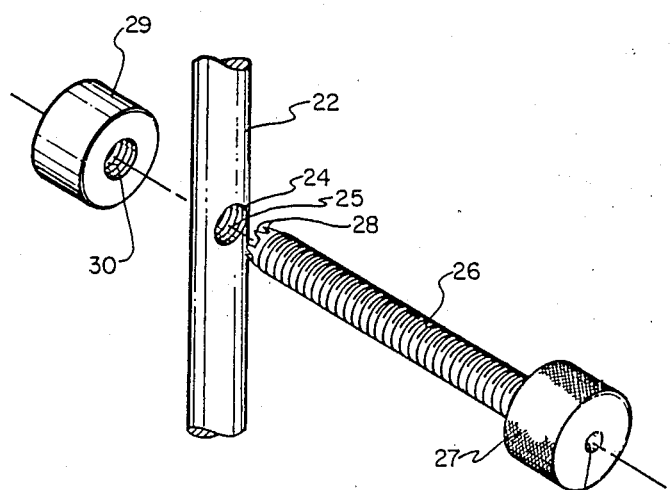
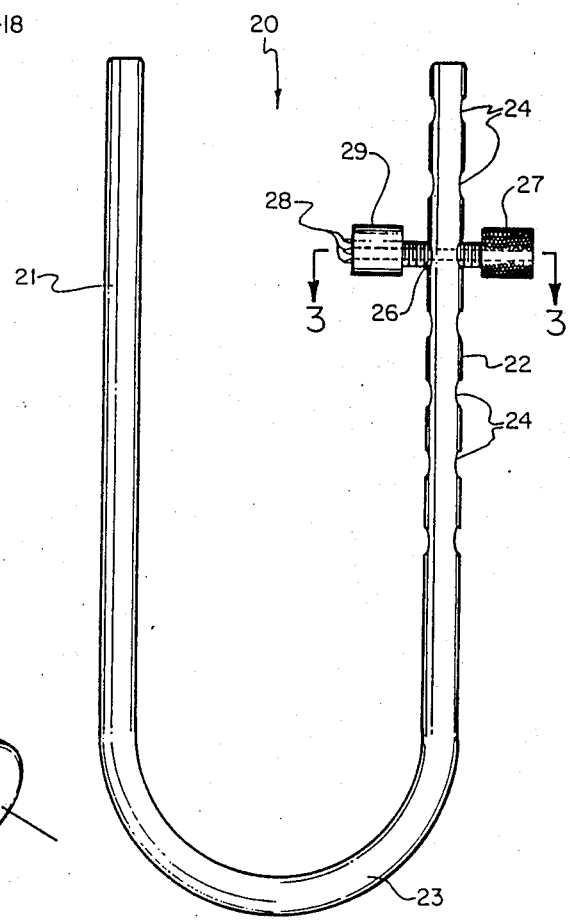

DRILL GUIDE

BACKGROUND OF THE INVENTION

1. Field of the Invention

This invention relates to surgical devices and particularly to devices that are used in arthroscopic surgical procedures that involve knee reconstructive surgery where a surgeon forms a ligament tunnel through the patient's knee to receive a prosthetic or biologic ligament replacing the anterior or posterior cruciate ligament.

2. Prior Art

The present invention is for use in anterior or posterior cruciate ligament repair and replacement surgery where tibial and femoral bony tunnel sections are formed for maintaining a ligament spanning the intra articular joint. In such procedure, with the knee bent appropriately, a straight bony tunnel is formed from a single incision to intersect both the ligament points of origin. The present inventor is an inventor of several patents and inventions that utilize such straight bony tunnels, including "Ligament Attachment Method and Apparatus", U.S. Pat. No. 4,772,286; "Ligament Attachment Anchor System", U.S. Pat. No. 4,870,957; and certain patent applications in an "Endosteal Fixation Stud and System" filed Jan. 16, 1990, Ser No. 465,914, and in a patent application for "Apparatus and Procedure for Verifying Isometric Ligament Position", filed Sept. 19, 1988, Ser. No. 246,324.

The present inventor is also an inventor of a drill guide, U.S. Pat. No. 4,901,711, that is utilized in a straight bony tunnel that is formed through both the distal femur and proximal cortexes that opens through incisions in the skin at both tunnel ends. This drill guide references a K-wire that is fitted through the bony tunnel and allows a transverse hole to be drilled from any point around the knee to exactly intersect the ligament tunnel. Whereas, the present invention is in a drill guide that needs to be installed through one ligament tunnel end only. Accordingly, the drill guide of the present invention is utilized in a straight ligament tunnel for guiding the drilling of transverse hole into the knee to intersect that bony tunnel as part of a surgical procedure that is minimally invasive.

Additional to the earlier drill guide of the present inventor, U.S. Pat. No. 4,901,711, set out above, other drill guide arrangements have been developed for utilization in cruciate ligament repair or replacement procedures. For example, patents to Sapeya, et al, U.S. Pat. No. 4,739,751; Cho, U.S. Pat. No. 4,257,411; Hourahane, et al, U.S. Pat. No. 4,535,768; Hourahane, U.S. Pat. No. 4,672,957; and a United Kingdom patent to Lovell, et al, No. 2,078,528, all show arrangements for drilling cruciate ligament tunnel sections through intra articular joint from a point on the proximal tibia or distal femur surfaces to intersect the end of a guide that is positioned on a cruciate ligament point of origin. Such earlier drill guides, of course, do not reference a straight ligament tunnel, as does the present invention, nor are they useful for drilling a transverse hole thereto. Additionally, patents to Seedholm, et al, U.S. Pat. No. 4,668,233, and a European patent application No. 0126529, show a prosthetic ligament and drill guide for preparing tibial and femoral tunnel sections.

None of which above cited references, are structurally or functionally like the drill guide of the present invention.

SUMMARY OF THE INVENTION

It is a principal object of the present invention in a improved drill guide is to provide a drill guide to enable a surgeon performing an endosteal cruciate ligament replacement surgical procedure to drill a transverse straight hole from without the knee to exactly intersect the bony cruciate ligament tunnel.

Another object of the present invention is to provide a drill guide for utilization in a straight bony ligament tunnel that is formed from a single incision through the intra articular joint, the drill guide for fitting through that single incision for use in forming a right angle hole or tunnel from without the knee to exactly intersect that bony ligament tunnel.

Still another object of the present invention is to provide drill guide function that is simple in its construction and is easy to use for forming an intersecting right angle tunnel or hole to a bony ligament tunnel.

The improved drill guide of the present invention is preferably for use in a arthroscopic surgical procedure where a straight cruciate ligament tunnel is formed, that extends across the knee intra articular joint that is to receive ligament secured therein. The drill guide of the present invention has a U-shaped body having with a pair of planar parallel legs, one of which legs is solid for fitting, in close fitting engagement, within the straight bony ligament tunnel. The other leg has a number of spaced tapped hole lateral holes therethrough, the longitudinal axis of each of which holes point at the solid leg. The tapped holes are for individually receiving a threaded barrel that is turned therethrough. The barrel has a longitudinal center bore of a diameter for receiving a desired diameter of drill that is turned therethrough.

The barrel includes, on one end thereof a wide cylindrical head for manual turning. A separate sleeve is provided that is center holed and tapped longitudinally that is for turning onto the end of the threaded barrel after it has been passed through one of the spaced tapped holes. The barrel, may include, on the end thereof that is turned through the sleeve, a plurality of spikes that extend axially from around that end that are for engaging the patient's skin when the barrel is turned towards the solid leg, which spikes are for maintaining the drill guide positioning.

In practice, a surgeon can fit the drill guide solid leg into one end of a prepared straight bony ligament tunnel and can then pivot the other holed leg around the knee to a certain desired longitudinal location across the intra articular knee joint. A particular tapped hole through the holed drill guide leg is selected to receive the barrel turned therethrough, the longitudinal bore of which barrel to point to the location on the knee to be drilled. The sleeve can then be turned into the barrel to where the barrel end spikes and barrel end extend beyond the sleeve end where at, the sleeve can be turned thereover to where the spikes extend beyond the sleeve face. The barrel is then turned to where the spikes engage the knee surface. A selected drill is then turned through the barrel longitudinal bore and through the patient's skin into the distal femur or proximal tibia to exactly intersect the straight bony ligament tunnel. Which hole or holes drilled into the ligament tunnel may be used for receiving screws, or like fastenings, that are turned into a ligament, a bone block ligament end, or the like, for maintaining the ligament end in that tunnel.

BRIEF DESCRIPTION OF THE DRAWINGS

These and other objects and features of the present invention in an improved drill guide will become more fully apparent from the following description in which the invention is described in detail in conjunction with the accompanying drawings.

FIG. 1 is a side elevation view of a patient's knee showing the distal femur, proximal tibia at the intra articular joint, wherefrom longitudinal section of covering skin has been removed, and a ligament tunnel has been formed through a single incision to the tibial anteromedial cortex, with one solid leg of a U-shaped drill guide of the present invention shown fitted therein and showing the other drill guide leg that is holed at spaced intervals aligned over the patient's knee, and showing a barrel turned through one of the drill guide leg holes with a conventional drill shown aligned with a bore of which barrel for turning into the knee;

FIG. 2, shows a side elevation view of the drill guide of FIG. 1;

FIG. 3, shows sectional view taken along the line 3—3 of FIG. 2; and

FIG. 4, shows an exploded sectional view of a section of the drill guide holed leg that is tapped and with the threaded barrel aligned for turning through that tapped hole and with a sleeve shown aligned for turning over that barrel.

DETAILED DESCRIPTION

FIG. 1 shows a side elevation view of an intra articular knee joint 10, with the distal femur 11 and proximal tibia 12 bones bent with a straight ligament tunnel 35 formed therein. The bony ligament tunnel, is shown in broken lines 15 as formed to an endosteum end 16 in the distal femur from an incision 18 to the anteromedial cortex of the proximal tibia at 14. The bony tunnel 15 extends through the origins of the anterior cruciate ligament and terminates at endosteum end 16, shown in broken line, proximate to the distal femur cortex. The ligament tunnel 15 is utilized in an arthroscopic surgical procedure for endosteally securing an end of an anterior cruciate ligament, either biologic or prosthetic, in the bone endosteum. The opposite ligament end extends beyond the tunnel 14, under tension and is either secured at that tunnel end or is fixed to the proximal tibia anteromedial cortex surface, as with a staple or staples, or the like, not shown.

Shown in FIG. 1, and an enlarged view of FIG. 2, the present invention is in a U-shaped solid drill guide 20, that has one solid leg 21 that is co-planar and parallel to a holed leg 22 with an arcuate yoke 23 therebetween and is preferably formed of a strong metal such a stainless steel. The solid leg 21 is shown as being straight and smooth and is to fit within the straight ligament tunnel 15, as shown in FIG. 1. In which fitting, the straight solid leg 21 end is inserted through an incision 18 in skin 17 and is directed into the proximal tibia anteromedial cortex end 14 of the ligament tunnel 15. The leg 21 is slid fully or partially therein, as required, to where a select hole 24 formed through the holed leg 22 is over a location on the knee surface wherethrough a surgeon wishes to drill a transverse tunnel or hole to intersect the ligament hole.

Shown in FIG. 2 the radius of the arcuate end 23 is selected so as to provide a desired spacing distance between the legs 21 and 22 that is convenient for allowing the holed leg 22 to rotate around the knee and is appropriately spaced from the knee for drilling to reach the solid leg 21 in the bony ligament tunnel.

The holed leg 22, as set out above, includes a plurality of equally spaced holes 24 whose longitudinal axis each point at the solid leg 21, and are formed at intervals along the leg 22. As shown in FIG. 1, the selection of a particular hole 24 provides the positioning of the point of origin of lateral or a transverse hole that is drilled to intersect the ligament tunnel 15.

Shown best in FIGS. 3 and 4, each hole 24 is threaded at 25 to receive a like threaded barrel 26 that is turned therethrough. Which barrel 26 includes, on one end, a broad head 27, that is preferably knurled or otherwise roughened to accommodate being manipulated by a surgeon operator. The opposite barrel 26 end includes a plurality of spaced spikes that extend axially outwardly at spaced intervals from around the barrel end. The barrel 26, as shown best in FIG. 2 and 3, is for turning through one of the holes 24, to where the spikes 28 and a leading end of that barrel extend beyond that hole. Which barrel threads at the leading end are to receive a threaded sleeve 29 that is turned axially thereover on threads 30. The sleeve 29 is turned to where a sleeve face 29a is spaced a distance back from the barrel spikes 28. So arranged, the spikes 28 will penetrate the patient's skin to a desired distance before the sleeve face 29a engages that skin surface. This spike 28 penetration and sleeve face 29a contact stabilizes the drill guide 20 to receive a drill 32 that is fitted through a longitudinal bore 31 formed through the barrel 26. Which barrel bore 31 is slightly larger than is the diameter of the drill 32. The barrel 26 longitudinal bore 31, as shown best in FIG. 3, extends the length thereof and allows the surgeon, by the selection of a size of barrel bore to select a particular drill 32 that is appropriate for the surgical procedure being practiced.

In practice, a surgeon inserts the drill guide solid 20 leg 21 into the ligament tunnel 15, as shown in FIG. 1, and selects a particular tapped hole 24 that is opposite to a location on the knee as the transverse hole point of origin. The barrel 26 fitted in that hole 24 is turned at broad head end 27, its spiked end passed through the tapped hole 24 to where the sleeve 29 can be turned over the barrel spiked end, with the spikes 28 extending a desired distance beyond the sleeve face 29a. The barrel 26 is then further turned to where the spikes 28 engage and travel somewhat into the patient's skin to a desired depth. Barrel 26 turning is continued to where the sleeve face 29a engages the patient's skin, thereby stabilizing the drill guide alignment. Which depth of spike 28 penetration may, as required, be to the distal femur or proximal tibia cortex surface.

With the barrel 26 at spikes 28 maintained to the patient's skin, as set out above, the surgeon can insert and turn a drill 32, as shown in FIG. 1, through the barrel bore 31 and into the knee to exactly intersect the ligament tunnel wherein the solid leg 21 is positioned. Which drill turning can be accomplished under fluoroscopic monitor control. Or, the drill 32 penetration can be set to reproduce the distance between the legs 21 and 22, taking into account the barrel 26 length, so that the drilled hole will just engage the tunnel side. With the selection of the appropriate diameter of the barrel bore 31, different size drills 32 can be utilized for turning to intersect the bony ligament tunnel.

The preferred embodiment of the present invention in an drill guide and its use has been shown and described herein. It should be apparent that this disclosure is made by way of example only and that variations and modifications to the apparatus and its use are possible within the scope of this disclosure without departing from the subject matter coming within the scope of following claims and a reasonable equivalency thereof, which claims I regard as my invention.

I claim:

1. A drill guide comprising, a rod that is bent upon itself into a U-shape, forming parallel co-planar legs, one of which legs is solid for fitting into a straight bony tunnel, and the other leg is holed laterally at spaced intervals therealong the longitudinal axis of each of which holes points to said solid leg which holes are tapped; and a barrel means has an longitudinal bore open therethrough, and has a threaded external surface for turning through one of said holes.

2. A drill guide as recited in claim 1, wherein the solid and holed legs are of equal length.

3. A drill guide as recited in claim 1, wherein the barrel means has a broad head on one end and includes a plurality of spaced spikes that extend axially from its other end; and a sleeve for fitting over said barrel means spiked end and turning onto said barrel means.

4. A drill guide as recited in claim 3, wherein the barrel means broad head end is knurled or otherwise roughened.

5. A drill guide as recited in claim 3, wherein the sleeve is holed and tapped axially for turning over the barrel means spiked end to where said spikes extend beyond a face of said sleeve.

* * * * *